US00PP08660P

United States Patent [19]

Voth et al.

[11] Patent Number: Plant 8,660

[45] Date of Patent: Mar. 29, 1994

[54] STRAWBERRY PLANT CALLED "CARLSBAD"

[75] Inventors: Victor Voth, Santa Ana; Douglas V. Shaw; Royce S. Bringhurst, both of Davis, all of Calif.

[73] Assignee: The Regents of the University of California, Oakland, Calif.

[21] Appl. No.: 41,638

[22] Filed: Apr. 1, 1993

[51] Int. Cl.[5] ..... A01H 5/00

[52] U.S. Cl. ..... Plt./49

[58] Field of Search ..... Plt. 48, 49

*Primary Examiner*—James R. Feyrer

*Attorney, Agent, or Firm*—Townsend and Townsend Khourie and Crew

[57] ABSTRACT

'Carlsbad' is a short-day (June-bearing) cultivar similar to 'Chandler' (U.S. Plant Pat. No. 5,262) but with larger total productivity, substantially larger early productivity, larger fruit, firmer fruit, and is a more vigorous plant.

2 Drawing Sheets

DESCRIPTION

This invention relates to a new and distinctive short-day type cultivar designated as 'Carlsbad', which resulted from a cross performed in 1988 between the cultivar 'Irvine' (U.S. Plant Pat. No. 7,172) and advanced selection Cal 85.218-605.

'Carlsbad' was first fruited at the University of California South Coast Research and Extension Center, near Irvine, Calif. in 1989, where it was selected, originally designated Cal 88.70-613, and propagated asexually by runners. Asexual propagules from this original source have been tested at the South Coast Research and Extension Center, the Watsonville Strawberry Research Facility, and to a limited extent in grower fields starting in 1990.

Figure 1:
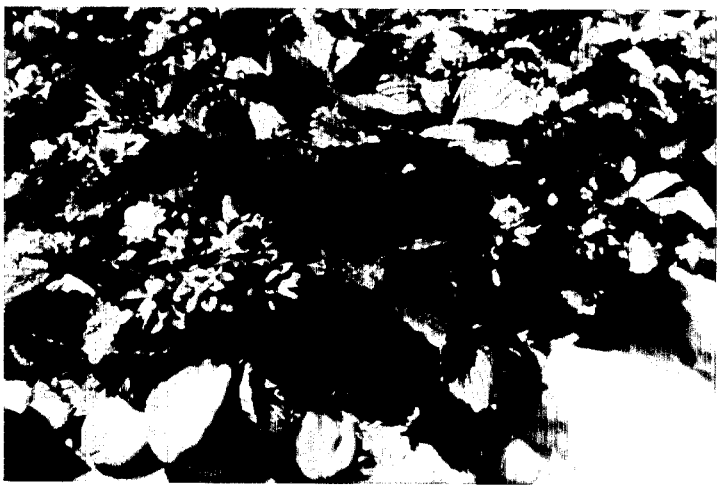
FIG. 1 shows the general flowering and fruiting characteristics of the plant.
Figure 2:
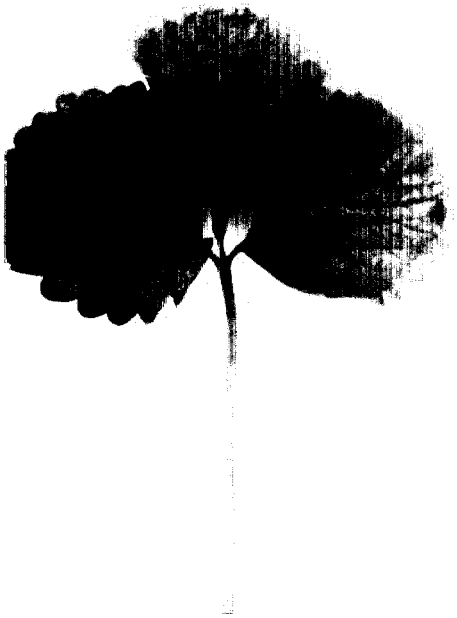
FIG. 2 shows a typical mature leaf during late spring.
Figure 3:
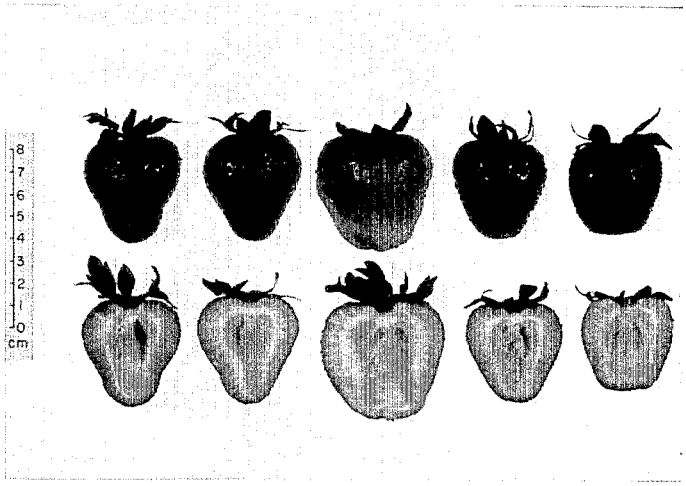
FIG. 3 shows representative mid-season fruit.

'Carlsbad' is typical of short-day types and products fruit over an extended period when treated appropriately in arid, subtropical climates. 'Carlsbad' differs from 'Irvine' in that 'Irvine' is a day-neutral type with essentially no photoperiodic flowering response and as compared with 'Carlsbad' is more difficult to grow. The production pattern for 'Carlsbad' is similar to that for 'Chandler', although it produces substantially greater quantities of early-season fruit. 'Carlsbad' will be of special interest for winter plantings, where 'Chandler' has been successful, and in summer plantings where 'Pajaro' has been successful.

Plants and foliage: Fruiting plants of 'Carlsbad' are larger, more erect, and more vigorous than plants of 'Chandler' (U.S. Plant Pat. No. 5,262), and are generally similar in form to plants of 'Oso Grande' (U.S. Plant Pat. No. 6,578). 'Carlsbad' forms branch crowns in greater quantity than 'Chandler' with similar branching to 'Oso Grande'. When propagated in the nursery, 'Carlsbad' has similar or greater runner production capacity compared with 'Chandler'. Comparative statistics for foliar characters, including leaf color, near mid-season are given for the three cultivars in Table 1 with visual comparisons of leaf color according to the Munsell color scale (Nickerson Color Fan) given in Table 5. Leaf color is distinctly lighter on the underside for 'Carlsbad'; the differential is larger than for 'Chandler' and similar to that for 'Oso Grande'. Individual leaflets for 'Carlsbad' are larger and somewhat more elongated than 'Chandler', and are less rounded than for 'Oso Grande'. Leaves (including petioles) are longer and much broader than for 'Chandler'. Petioles are thicker and stiffer than those of 'Chandler' and are similar to those of 'Oso Grande'. Paired stipules, borne in a median position on the petiole, appear as small, stalked, ovate to heart-shaped structures on most leaves for 'Carlsbad' and the comparison cultivars. Stipule size varies greatly both within and among individual plants for 'Carlsbad', and one or both stipules may be absent or may be abscise as the leaf matures. Leaf and petiole pubescence characters for 'Carlsbad' are similar to those for 'Oso Grande', except that tomentum on leaves are less dense. Also, leaves for 'Carlsbad' are darker than leaves of 'Chandler' and similar in color but slightly darker than those of 'Oso Grande'. Visual comparisons of fruit color according to the Munsel color scale (Nickerson Color Fan) are given in Table 5. 'Carlsbad' has flat (occasionally concave) leaves, which are easily distinguished from 'Chandler', and are similar in convexity to 'Oso Grande'.

Isozymes in leaf extracts: 'Carlsbad' has been classified for three isozyme systems using starch gel electrophoresis (Table 2): Phosophoglucoisomerase (PGI), Leucine Aminopeptidase (LAP), and Phosphoglucomutase (PGM). It is distinguishable from all other short-day cultivars released to date. For electrophoretic procedures see: J. Amer. Soc. Hort. Sci. 106:684-687.

Disease and pest reaction: 'Carlsbad' is moderately resistant to common leaf spot (*Ramularia tulasnei*) and powdery mildew (*Sphaerotheca macularis*). When treated properly, it has equal or greater tolerance to two-spotted spidermites (*Tetranychus urticae*) than 'Chandler'. 'Carlsbad' is tolerant to strawberry viruses encountered in California.

TABLE 1

Foliar characteristics for 'Carlsbad', 'Chandler', and 'Oso Grande'.

| | Cultivar | | |
|---|---|---|---|
| Foliar Character | 'Carlsbad' | 'Chandler' | 'Oso Grande' |
| Mid-tier leaflet | | | |
| Length (mm) | | | |
| mean | 90.4 | 82.4 | 77.2 |

TABLE 1-continued

Foliar characteristics for 'Carlsbad', 'Chandler', and 'Oso Grande'.

| Foliar Character | Cultivar 'Carlsbad' | 'Chandler' | 'Oso Grande' |
|---|---|---|---|
| range | 85–97 | 78–94 | 75–80 |
| Width (mm) | | | |
| mean | 75.8 | 71.4 | 67.6 |
| range | 65–82 | 63–88 | 62–71 |
| Mid-tier leaf | | | |
| Length (mm) | | | |
| mean | 261.0 | 244.2 | 191.6 |
| range | 257–269 | 218–262 | 170–200 |
| Width (mm) | | | |
| mean | 162.4 | 148.0 | 137.2 |
| range | 148–175 | 132–158 | 130–149 |
| Leaf color (CIELAB)* | | | |
| L* | | | |
| mean | 30.0 | 31.4 | 31.9 |
| range | 27.7–31.8 | 27.1–33.3 | 29.9–33.0 |
| a* | | | |
| mean | −6.7 | −8.0 | −5.3 |
| range | −3.8–−8.8 | −5.2–−8.2 | −4.2–−8.3 |
| b* | | | |
| mean | 14.2 | 16.0 | 15.5 |
| range | 10.0–17.5 | 12.9–21.4 | 12.5–20.6 |
| # leaflets/leaf | 3 | 3 | 3 |
| Leaf convexity | flat/slight concave | concave | concave |
| Serrations | | | |
| number | few | many | moderate |
| shape | semi-round | semi-pointed | semi-round |
| Leaf pubescence | moderate | moderate/ sparse | moderate/ heavy |
| Petiole pubescence | | | |
| density | heavy | heavy | heavy |
| direction | perpendicular | acropetal | perpendicular |

*CIELAB is the abbreviation of the international color system known as "Commission Internationale De L'Eclairage" 1978. Recommendations on uniform color spaces — color difference equations, psychometric color terms, Supplement No. 2 to CIE Publication No. 15. PARIS. 2

TABLE 2

Isozyme phenotypes for 'Carlsbad', 'Chandler', and 'Oso Grande'.

| Locus | Cultivar 'Carlsbad' | 'Chandler' | 'Oso Grande' |
|---|---|---|---|
| PGI | A2 | A1 | A2 |
| LAP | B3 | B3 | B3 |
| PGM | C1 | C1 | C2 |

Flowering, fruiting, fruit, and production characteristics: Comparative statistics for flower and fruit characters, including fruit color, near mid-season are given for 'Carlsbad', 'Chandler' and 'Oso Grande' in Table 3. The primary flowers for 'Carlsbad' are slightly larger than those of 'Chandler' and 'Oso Grande', whereas the sepals are substantially larger than for the comparison cultivars. Each primary flower has 5–7 petals. The calyx for 'Carlsbad' is usually even with the shoulder of the fruit, but is occasionally slightly indented and ocassionally necked. The primary fruit shape for 'Carlsbad' is a very flat conic, with secondary fruit usually a blocky conic. External fruit color for 'Carlsbad', is lighter than 'Chandler', and 'Oso Grande'. and the fruit somewhat less glossy than 'Chandler'; internal color is lighter than 'Chandler' and darker than for 'Oso Grande'. Achenes vary from yellow to dark red, and are even with the fruit surface or slightly extruded.

'Carlsbad' has been tested under a variety of cultural regimes, and optimal performance is obtained when nursery treatments, pre-plant chilling regimes, plant densities, and nutritional programs similar to those that optimize performance for 'Chandler' are used. In general, 'Carlsbad' is more adapted to early-season planting with less supplemental chilling than 'Chandler'.

When treated with appropriate planting regimes, 'Carlsbad' has larger fruit and produces greater yields than 'Chandler' or 'Oso Grande' (Table 4). 'Carlsbad' is similar to 'Chandler' and 'Oso Grande' in its production pattern, although it produces substantially more early-season fruit than either cultivar (with conventional winter planting). Commercial appearance ratings have been comparable to or better than those for 'Chandler'. Fruit of 'Carlsbad' is firmer than that for 'Chandler'; 'Carlsbad' is about as firm as 'Oso Grande'. Subjectively, 'Carlsbad' has very good flavor, somewhat less aromatic than 'Chandler', but with better acid balance and more aromatic components than 'Oso Grande'. The fruit will be outstanding for both fresh market and processing, due to its firm flesh and relatively dark internal color, and will be useful for home garden purposes.

TABLE 3

Flower and fruit characters for 'Carlsbad', 'Chandler', and 'Oso Grande'.

| Character | Cultivar 'Carlsbad' | 'Chandler' | 'Oso Grande' |
|---|---|---|---|
| # petals | | | |
| mean | 6.2 | 6.6 | 5.0 |
| range | 5–7 | 6–8 | 5–5 |
| Flower position (relative to foliage) | exposed | even/ exposed | exposed |
| Calyx diam. (mm) | | | |
| mean | 63.8 | 47.7 | 34.1 |
| range | 56–70 | 45–53 | 27–38 |
| Corolla diam. (mm) | | | |
| mean | 40.7 | 39.3 | 32.2 |
| range | 37–44 | 36–46 | 27–41 |
| Fruit shape | | | |
| length/width ratio | 1.02 | 1.33 | 1.06 |
| subjective | flat/conic | flat conic | blocky/conic |
| Calyx position | even/slight indent | even/slight neck | even/slight indent |
| Seed position | slight extrude | even/slight indent | even |
| Fruit color (CIELAB) | | | |
| external | | | |
| L* | 25.4 | 23.6 | 22.4 |
| a* | 29.9 | 38.5 | 31.2 |
| b* | 16.3 | 14.8 | 17.2 |
| internal | | | |
| L* | 47.8 | 46.2 | 54.1 |
| a* | 37.9 | 39.1 | 30.4 |
| b* | 28.9 | 29.4 | 22.7 |

TABLE 4

Performance for selection 'Carlsbad' compared with 'Oso Grande' and 'Chandler' at the South Coast Research and Extension Center in 1991. All plants were dug from the South Coast nursery on October 1 and planted October 2 (68"/4-row beds, 23,061 plants/A, 100 g/plant = 425 Crates/A).

| | Yield To 4/1 (g/plant) | Total Yield (g/plant) | Size (g/fruit) | Appearance Score | Firmness |
|---|---|---|---|---|---|
| 'Carlsbad' | 510 | 2,308 | 27.2 | 4.2 | 4.7 |
| 'Chandler' | 463 | 1,738 | 23.3 | 3.9 | 4.0 |
| 'Oso Grande' | 530 | 1,675 | 25.0 | 3.8 | 4.9 |

TABLE 5

Munsell color classification for leaf and fruit characters.

| Item | Munsell Leaf Color Classes Upper (Adaxial) | Munsell Leaf Color Classes Lower (Abaxial) | Munsell Fruit Color Classes External | Munsell Fruit Color Classes Internal |
|---|---|---|---|---|
| Chandler | 5GY 4/3 | 5GY 5/6 | 5R 5/13 | 7R 5/13 |
| | 5GY 5/6 | | 5R 4/12 | |
| Oso | 5GY 4/3 | 5GY 5/6 | 5R 5/13 | 7.5R 7/9 |

TABLE 5-continued

Munsell color classification for leaf and fruit characters.

| Item | Munsell Leaf Color Classes Upper (Adaxial) | Munsell Leaf Color Classes Lower (Abaxial) | Munsell Fruit Color Classes External | Munsell Fruit Color Classes Internal |
|---|---|---|---|---|
| | 5GY 3/2 | 7.5GY 6/8 | 7.5R 5/13 | 7.5R 6/12 |
| Carlsbad | 7.5GY 4/4 | 7.5GY 5/8 | 7.5R 5/13 | 7.5R 6/12 |
| | 5GY 4/3 | 7.5GY 4/7 | 7.5R 4/11 | 7.5R 5/13 |

We claim:

1. The new and distinct variety of strawberry plant illustrated and described and having the characteristics above enumerated.

* * * * *